United States Patent [19]
Hoshino et al.

[11] Patent Number: 5,922,581
[45] Date of Patent: Jul. 13, 1999

[54] PROCESS FOR THE PRODUCTION OF D-BIOTIN

[75] Inventors: Tatsuo Hoshino, Kamakura; Akifumi Noro, Fujisawa; Masaaki Tazoe, Yokohama, all of Japan

[73] Assignee: Roche Vitamins Inc., Parsippany, N.J.

[21] Appl. No.: 08/833,411

[22] Filed: Apr. 4, 1997

[30] Foreign Application Priority Data

Apr. 6, 1996 [EP] European Pat. Off. .............. 96105530

[51] Int. Cl.⁶ .............................. C12N 1/00; C12P 17/10; C12P 17/18
[52] U.S. Cl. ...................... 435/117; 435/119; 435/252.1; 435/822
[58] Field of Search ................................ 435/252.1, 822, 435/117, 119

[56] References Cited

FOREIGN PATENT DOCUMENTS

| 0 532 426 | 3/1993 | European Pat. Off. . |
| 152 495 | of 1983 | Japan . |
| 27 980 | of 1990 | Japan . |
| 169 180 | of 1992 | Japan . |
| 2 216 530 | 10/1989 | United Kingdom . |

OTHER PUBLICATIONS

CAPLUS Abstract 1984:99663 –100:99663 Shaw et al., "The Vitamin requirements of *Kurthia zopfil* and *Kurthia gibsonii*" "Syst. Appl. Microbio." (1983) 4(4), pp. 439–443.

Derwent Abstract No. AN–96–500371 (Abstract of JP 08 256 785A). Published Oct. 8, 1996.
*Agric. Biol. Chem.*, 47(5):1011–1016 (1983).
*Bergey's Manual of Systematic Bacteriology*, 9th ed., vol. 2, p. 1255 (1984).
*Biochem. Biophys. Res. Comm.*, 18:788 (1965).
*J. Microbiological Methods*, 6:237–245 (1987).
*Proc. Soc. Exp. Biol. Med.*, 56:95–98 (1944).

*Primary Examiner*—Herbert J. Lilling
*Attorney, Agent, or Firm*—George W. Johnston; Dennis P. Tramaloni; Eileen M. Ebel

[57] ABSTRACT

A process for producing d-biotin comprises cultivating a microorganism of the genus Kurthia and which is resistant to biotin antimetabolites and capable of producing d-biotin in a medium under aerobic conditions, and separating the resulting d-biotin from the fermentation broth. The cultivation medium suitably contains an assimilable carbon source, a digestible nitrogen source, inorganic salts and other nutrients necessary for the growth of the microorganism at a pH of about 5–9, temperature of about 10–40° C. and for a duration of about 1–10 days. The preferred microorganism are Kurthia sp. 538-KA26, 538-17H4, 538-51F9 and 538-2A 13 (DSM No. 10609, 10608, 10610 and 10607, respectively), which are also new, and as such represent a further aspect of the present invention. The so-produced d-biotin is one of the essential vitamins for the nutrition of animals, plants and microorganisms, and is important as a medicine or food additive. It is produced in particularly high yield by the process of the present invention.

15 Claims, No Drawings

PROCESS FOR THE PRODUCTION OF D-BIOTIN

BACKGROUND OF THE INVENTION

This invention relates to a process for the production of d-biotin by fermentation.

d-Biotin is one of the essential vitamins for the nutrition of animals, plants and microorganisms, and is very important as a medicine or food additive. The present invention enables the production of d-biotin by fermentation to occur in high yield.

There are many studies on the fermentative production of d-biotin. Bacillus strains resistant to biotin antimetabolites [see Japanese Patent Publication (Kokai) No. 152495/1983] and Serratia strains resistant to biotin antimetabolites (Japanese Kokai No. 27980/1990) are capable of producing 0.6–4.0 mg/L and 4.3–22 mg/L of d-biotin, respectively. However, the production of d-biotin by microorganisms belonging to the genus Kurthia resistant to biotin antimetabolites has never been reported.

SUMMARY OF THE INVENTION

The present invention enables large amounts of d-biotin to be accumulated. It has been found that microorganisms belonging to the genus Kurthia and which are resistant to biotin antimetabolites, e.g. acidomycin (hereinafter referred to as ACM), 5-(2-thienyl)-valeric acid (TVA), α-methyl dethiobiotin (MeDTB), 2-methyl ACM, amiclenomycin, bisnorbiotinol and mixtures thereof, are capable of accumulating large amounts of d-biotin in the culture broth and that the d-biotin can be recovered therefrom in good purity. In fact, it is possible to produce d-biotin by the present invention in about 5 to 200 times higher yields than those achieved with known methods utilizing strains belonging to the genus Bacillus or Serratia. Thus, according to the present invention, there is provided a process for producing d-biotin which comprises cultivating a microorganism belonging to the genus Kurthia, which microorganism is resistant to biotin antimetabolites and capable of producing d-biotin in a medium under aerobic conditions, and separating the resulting d-biotin from the fermentation broth.

DETAILED DESCRIPTION OF THE INVENTION

Microorganisms which can be used in accordance with the present invention include all the d-biotin-producing microorganisms which belong to the genus Kurthia [see Bergey's Manual of Systematic Bacteriology, $9^{th}$ ed., vol. 2, 1255 (1984)] and are resistant to biotin antimetabolites, such as those mentioned above. The above-mentioned microorganisms can be obtained efficiently by treating strains belonging to the genus Kurthia as parent strains with a mutagen, e.g. N-methyl-N'-nitro-N-nitrosoguanidine (hereinafter referred to as NTG), ethyl methane sulfonate, acridine orange, UV- or X-rays.

Any strain belonging to the genus Kurthia can be used as a parent strain for preparing the microorganisms used in accordance with the present invention. The microorganisms belonging to the genus Kurthia may be isolated from natural sources or may be purchased from culture collections. Kurthia sp. 533-6 (DSM No. 9454) is preferably used for the present invention. The microorganisms which are capable of producing large amounts of d-biotin can be obtained by isolating a microorganism belonging to the genus Kurthia and being resistant to biotin antimetabolites, such as those mentioned above. For example, a mutant of Kurthia sp. 538-6 (DSM No. 9454) producing large amounts of d-biotin was isolated as described below.

The content of d-biotin accumulated in the culture broth can be assayed by the turbidity method [J. Microbiological Methods, 6, 237–245 (1987)] by means of *Lactobacillus plantarum* ATCC 8014 [Proc. Soc. Exp. Biol. Med., 56, 95–98 (1944)].

(1) Isolation of an ACM-resistant mutant capable of producing large amounts of d-biotin.

Cells of Kurthia sp. 538-6 (DSM No. 9454) cultured in a liquid medium were harvested by centrifugation, washed and suspended in saline. The mutagenesis was carried out by the method of Adelberg et al. [Biochem. Biophys. Res. Comm., 18, 788 (1965)] which is herein incorporated by reference and as described below. The cells were treated with 50–300 μg/ml of NTG in 100 mM Tris-HCl buffer, pH 8.0, with shaking. After the treatment, the cells were washed and resuspended in saline. The washed cells were spread onto agar plates of a d-biotin-free synthetic medium comprising 20 g of glycerol, 5 g of vitamin-free casamino acids (Difco), 2 g of $K_2HPO_4$, 1 g of $KH_2PO_4$, 0.5 g of $MgSO_4 \cdot 7H_2O$, 0.01 g of $FeSO_4 \cdot 7H_2O$, 0.01 g of $MnSO_4 \cdot 5H_2O$ and 100 μg of thiamine·HCl in 1,000 ml of distilled water (hereinafter referred to as BM) with 100 μg/ml of ACM. After incubation large colonies grown were inoculated on assay plates containing Lactobacillus plantarum ATCC 8014 as a biotin indicator strain. After incubation at 37° C., the diameters of growth halos, which depended on the amount of d-biotin, were measured. From the result, a colony producing the largest halo was obtained and designated Kurthia sp. 538-KA 26.

(2) Isolation of an ACM and TVA-resistant mutant capable of producing large amounts of d-biotin Kurthia sp. 538-KA 26 was cultured and the cells were treated with NTG in a similar manner as described in (1) above. The treated cells were cultured in a d-biotin-free synthetic medium composed of 20 g of glycerol, 3 g of $(NH_4)_2SO_4$, 2 g of $K_2HPO_4$, 1 g of $KH_2PO_4$, 0.5 g of $MgSO_4 \cdot 7H_2O$, 0.01 g of $FeSO_4 \cdot 7H_2O$, 0.01 g of $MnSO_4 \cdot 5H_2O$, and 100 μg of thiamine·HCl in 1,000 ml of distilled water (hereinafter referred to as MM) with 200 μg/ml of ACM and 200 μg/ml of TVA, and then transferred serially several times in a fresh medium with 200 μg/ml of ACM and 200 μg/ml of TVA at 2 to 3 day intervals. The resulting enriched cultures were diluted and spread onto agar plates of MM containing 200 μg/ml of ACM and 200 μg/ml of TVA. After incubation, large colonies grown were inoculated onto the assay plates with *Lactobacillus plantarum* ATCC 8014 in a similar manner as described in (1) above. After incubation, the diameters of growth halos were measured. From the result, a colony producing the largest halo was obtained and designated Kurthia sp. 538-17H4.

(3) Isolation of an ACM, TVA and MeDTB-resistant mutant capable of producing large amounts of d-biotin Kurthia sp. 538-17H4 was cultured and the cells were treated with NTG in a similar manner as described in (1) above. The treated cells were spread onto agar plates of BM containing 100 μg/ml of ACM. After incubation, the colonies were inoculated onto agar blocks of a production medium containing 0.5 μg/ml of d-dethiobiotin and 80 μg/ml of MeDTB in a plate. After incubation, the agar blocks were irradiated with UV light, and then transferred on the assay plates with *Lactobacillus plantarum* ATCC 8014. After incubation, the diameters of growth halos were measured. From the result, a colony producing the largest halo was obtained and designated Kurthia sp. 538-51F9.

Furthermore, in a similar manner as described in the preceding paragraph, a mutant resistant to 150 μg/ml of MeDTB was screened. From the study, a colony producing a halo larger than Kurthia sp. 538-51F9 was obtained and designated Kurthia sp. 538-2A13.

The process of the present invention is suitably effected by cultivating (incubating) the microorganism in a medium containing an assimilable carbon source, a digestible nitrogen source, inorganic salts and other nutrients necessary for the growth of the microorganism. As a carbon source, for example, glucose, fructose, starch, lactose, maltose, galactose, sucrose, dextrin, glycerol or millet jelly, preferably glycerol or glucose, may be employed. As a nitrogen source, for example, peptone, soybean powder, corn steep liquor, meat extract, ammonium sulfate, ammonium nitrate, urea or a mixture thereof may be employed, preferably peptone. Furthermore, as trace elements sulfates, hydrochlorides or phosphates of calcium, magnesium, zinc, manganese, cobalt and iron may be employed. Particularly suitable as inorganic salts are monopotassium phosphate, magnesium sulfate, ferrous sulfate and manganese sulfate. And, if necessary, conventional nutrient factors or an antifoaming agent, such as animal oil, vegetable oil or mineral oil can also be added. The pH of the culture medium is conveniently about 5.0 to 9.0, preferably 6.5 to 7.5. The cultivation temperature is suitably about 10 to 40° C., preferably 26 to 30° C. The cultivation time may be about 1 to 10 days, preferably 2 to 7 days, most preferably about 2 to 4 days (48 to 96 hours). In the cultivation, aeration and agitation usually give favorable results.

After the cultivation the d-biotin produced may be separated from the culture broth and purified. For this purpose a process generally used for extracting a certain product from the culture broth may be applied by utilizing various properties of d-biotin. Thus, for example, the cells are removed from the culture broth, the desired substance in the filtrate is absorbed on active carbon, then eluted and purified further with an ion exchange resin. Alternatively, the culture filtrate is applied directly to an ion exchange resin and, after the elution, the desired product is recrystallized from a mixture of alcohol and water.

The microorganisms used according to the present invention include all the strains resistant to ACM, TVA, MeDTB, 2-methyl ACM, amiclenomycin, bisnorbiotinol, or mixtures thereof belonging to the genus Kurthia and being capable of producing d-biotin. Among strains of genus Kurthia, particularly preferred strains are Kurthia sp. 538-KA 26, Kurthia sp. 538-17H4, Kurthia sp. 538-51F9 and Kurthia sp. 538-2A13, which were deposited at the DSM (Deutsche Sammlung von Mikroorganismen und Zellkulturen GmbH) in Braunschweig, Germany under DSM Nos. 10609, 10608, 10610 and 10607, respectively, on Mar. 26, 1996. These preferred strains are also new, and are also embraced per se by the present invention.

The present invention will be explained in more detail by the following Examples; however, it should be understood that the present invention is not limited to those particular Examples.

EXAMPLE 1

One loopful of Kurthia sp. 538-6 (DSM No. 9454) grown on agar of the medium composed of 1% bouillon (Kyokutoh Seiyaku Co. Ltd., Japan) (referred to as NB hereinafter) was inoculated into a 500-ml flask containing 50 ml of NB medium, and then the flask was shaken on a rotary shaker (180 rpm) at 28° C. After cultivation for 13.5 hours, the cells of the culture broth were harvested by centrifugation at 7,500 rpm for 10 minutes, washed twice with sterile saline and suspended in 20 ml of sterile water. Tubes containing 5 ml of the reaction mixture composed of 50–300 μg/ml of NTG and $1 \times 10^7$ cells per ml in 100 mM Tris-HCl buffer (pH 8.0) were incubated with reciprocal shaking (285 rpm) at 28° C. for 30 minutes. The cells were washed twice with 5 ml of sterile saline and suspended in 5 ml of saline. The cell suspensions were serially diluted $10^{-1}$–$10^{-7}$ in sterile saline and spread onto BM agar with 100 μg/ml of ACM. After incubation for 3 days at 28° C., the d-biotin productivity of each colony grown was determined by the agar plate method containing Lactobacillus plantarum ATCC 8014 as described below. Seven hundred and fifty colonies were transferred with toothpicks onto the assay plates containing Lactobacillus plantarum ATCC 8014. After incubation overnight at 37° C., the diameters of growth halos, which depended on the amount of d-biotin, were measured. As a result, Kurthia sp. 538-KA 26 (DSM No. 10609), producing the largest halo, was obtained.

One loopful of Kurthia sp. 538-KA 26 cells grown on BM agar with 100 μg/ml of ACM was inoculated into a tube containing 5 ml of production medium composed of 2% glycerol, 4% proteose peptone (Nippon Seiyaku Co. Ltd., Japan), 0.1% $KH_2PO_4$, 0.05% $MgSO_4 \cdot 7H_2O$, 0.001% $FeSO_4 \cdot 7H_2O$ and 0.001% $MnSO_4 \cdot 5H_2O$ and then the tube was shaken on a reciprocal shaker (285 rpm) at 28° C. After cultivation for 3 days, the content of d-biotin in the supernatant of the culture broth was assayed by the turbidity method with Lactobacillus plantarum ATCC 8014 as described below. The supernatant and standard solutions of d-biotin (0–10 mg per liter) were diluted 1.25–$10^{-3}$ in distilled water. Fifty microliters of the diluted solution and 5 ml of distilled water were added to tubes in this order. After autoclaving at 120° C. for 10 minutes, 5 ml of the assay medium for d-biotin (Nissui Co. Ltd., Japan) with Lactobacillus plantarum ATCC 8014 were added to the tubes and then the tubes were incubated in an upright position at 37° C. After incubation for 21 hours, the cell growth was stopped by adding 5 ml of 0.2 N hydrochloric acid, and then the turbidity of the samples was measured at 660 nm. The amount of d-biotin in a sample was determined by comparing the turbidity of the sample with the standard growth curve of Lactobacillus plantarum ATCC 8014. As a result, the supernatant of 3 day-culture broth contained 3.9 mg of d-biotin per liter. Kurthia sp. 538-KA 26 (DSM No. 10609) produced about 3,900 times more biotin than the parent strain, Kurthia sp. 538-6 (DSM No. 9454).

EXAMPLE 2

In a similar manner as described in Example 1, the cells of strain 538-KA 26 (DSM No. 10609) were treated with NTG, and the cells resistant to ACM and TVA were enriched as described below. The washed cells after NTG treatment were inoculated into tubes containing 5 ml of BM medium with 100 μg/ml of ACM, and the tubes were shaken on a reciprocal shaker (285 rpm) at 28° C. After overnight incubation, the culture broth was inoculated to give a turbidity at 600 nm of approximately 0.03 into a tube containing 5 ml of MM with 200 μg/ml of ACM and 200 μg/ml of TVA. The tubes were shaken at 28° C. and their contents allowed to grow until the culture became turbid. This enrichment was repeated in tubes containing the fresh MM medium with 200 μg/ml of ACM and 200 μg/ml of TVA at 2 or 3 day-intervals. After 3 repeats, the cultures were diluted in saline and spread onto agar of the same medium. After incubation for 3–4 days at 28° C., the d-biotin productivity was determined in 650 colonies on assay plates with *Lactobacillus plantarum* ATCC 8014. As a result, Kurthia sp. 538-17H4 (DSM No. 10608), producing the largest halo, was obtained.

One loopful of Kurthia sp. 538-17H4 (DSM No. 10608) grown on BM agar with 100 μg/ml of ACM was inoculated into a tube containing 5 ml of BM medium with 500 μg/ml of ACM, and then the tube was shaken at 28° C. After overnight incubation, 1 ml of the culture broth was transferred into a flask containing 50 ml of the production medium composed of 4% glycerol, 4.5% proteose peptone, 0.1% $KH_2PO_4$, 0.05% $MgSO_4·7H_2O$, 0.05% $FeSO_4·7H_2O$, 0.001% $MnSO_4·5H_2O$ and one drop of antifoam CA-115 (Nippon Yushi Co. Ltd., Japan), and then the flask was shaken at 28° C. After cultivation for 72 hours, the content of d-biotin in the supernatant of the culture broth was assayed by the turbidity method with *Lactobacillus plantarum* ATCC 8014. As a result, the supernatant contained 26.3 mg of d-biotin per liter. Kurthia sp. 538-17H4 (DSM No. 10608) produced about 6.7 times as much biotin as the parent strain, Kurthia sp. 538-KA 26 (DSM No. 10609), did.

EXAMPLE 3 d-Biotin was recovered from the culture broth of Kurthia sp. 538-17H4 (DSM No. 10608). The d-biotin concentration at each purification step was followed by the turbidity method with *Lactobacillus plantarum* ATCC 8014. One liter of the 72 hour-culture broth having d-biotin activity of 25.7 mg/L against *Lactobacillus plantarum* ATCC 8014 was centrifuged at 7,500 rpm for 10 minutes. The supernatant was applied to a column (3.6×42 cm) packed with 380 ml of charcoal (Wako Pure Chemical Industries., Co. Ltd., Japan). After washing with 500 ml of deionized water, the column was developed with 500 ml of the ethanolic ammonia solution composed of 474 ml of 50% ethanol and 26 ml of 25% ammonia. Three hundred milliliters of the eluent having d-biotin activity of 82.1 mg/L against *Lactobacillus plantarum* ATCC 8014 were concentrated to 50 ml under reduced pressure. The concentrate was applied to a column (2.6×38 cm) packed with 190 ml of Dowex 1×4 (formate form, 100–200 mesh, Dow Chemical Co. Ltd., U.S.A.), and then the column was washed with 200 ml of 0.05 M formic acid. The column was developed with 250 ml of the starting buffer of 0.1 M formic acid and followed by the linear gradient of 250 ml each of 0.1 and 0.35 M formic acid. One hundred and sixty milliliters of the eluent having d-biotin activity of 144.8 mg/L against *Lactobacillus plantarum* ATCC 8014 were concentrated under reduced pressure to obtain 17.6 mg of white powder. This was crystallized from a mixture of ethanol and water to obtain 15.1 mg of white needles having a melting point of 232° C. The melting point, Rf value on T.L.C. (solvent system: ethyl acetate/methanol= 10/1, Kieselgel 60 F254, E. Merck), infrared spectrum and NMR spectrum of the sample coincided with those of authentic d-biotin (Sigma Co. Ltd., U.S.A.).

EXAMPLE 4

In a similar manner as described in Example 1, the cells of Kurthia sp. 538-17H4 (DSM No. 10608) were treated with NTG, and a MeDTB-resistant mutant was then screened by the method as described below. After the treated cells had been cultured overnight at 28° C. in BM medium with 100 μg/ml of ACM, the culture was serially diluted $10^{-1}$ to $10^{-7}$ in sterile saline and spread onto BM agar with 80 μg/ml of ACM. After incubation for 2–3 days at 28° C., 19,500 colonies were inoculated onto agar blocks of the production medium composed of 2% glycerol, 2% proteose peptone, 0.1% $KH_2PO_4$, 0.05% $MgSO_4·7H_2O$, 0.05% $FeSO_4·7H_2O$, 0.001% $MnSO_4·5H_2O$ and 1.5% agar supplemented with 0.5 μg/ml of d-dethiobiotin and 80 μg/ml of MeDTB in plates. After incubation for 2 days at 28° C., the agar blocks were irradiated with UV light for 2 hours, and then transferred on the assay plates of Lactobacillus plantarum ATCC 8014. The assay plates were incubated at 37° C. for 19 hours, and then the diameters of halos were measured. As the result, Kurthia sp. 538-51F9 (DSM No. 10610), producing the largest halo, was obtained.

Kurthia sp. 538-51F9 (DSM No. 10610) grown on BM agar with 100 μg/ml of ACM was cultured at 28° C. in a tube containing 5 ml of BM medium with 500 μg/ml of ACM. After overnight cultivation, the cells were harvested by centrifugation and suspended in the 10% glycerol solution. One milliliter of the cell suspension was transferred into a flask containing 50 ml of the production medium composed of 6% glycerol, 5.5% proteose peptone ,0.1% $KH_2PO_4$, 0.05% $MgSO_4·7H_2O$, 0.05% $FeSO_4·7H_2O$, 0.001% $MnSO_4·5H_2O$ and one drop of antifoam CA-115 (hereinafter referred to as FM 1), and then the flask was cultured at 28° C. After cultivation for 72 hours, the content of d-biotin in the supernatant of the culture broth was assayed by the turbidity method with *Lactobacillus plantarum* ATCC 8014. As the result, the supernatant contained 41.5 mg of d-biotin per liter. Kurthia sp. 538-51F9 (DSM No. 10610) produced about 1.6 times as much biotin as the parent strain, Kurthia sp. 538-17H4 (DSM No. 10608), did.

EXAMPLE 5

A mutant more resistant to MeDTB was derived from Kurthia sp. 538-51F9 (DSM No. 10610). In a similar manner as described in Example 1, the cells of Kurthia sp. 538-51 F9 (DSM No. 10610) were treated with NTG, and then mutants resistant to 150 μg/ml of MeDTB were screened by the method similar to that described in Example 4 except for the concentration of MeDTB in agar blocks. As a result, Kurthia sp. 538-2A13 (DSM No. 10607), producing the largest halo, was thus obtained.

In a similar manner as described in Example 4, Kurthia sp. 538-2A13 (DSM No. 10607) was cultured at 28° C. in a flask containing 50 ml of FM 1 medium. After cultivation for 24 hours, 5 ml of the sterile medium containing 40% glycerol and 20% proteose peptone were fed, and the cultivation was continued. After cultivation for 120 hours, the content of d-biotin in the supernatant of the culture broth was assayed by the turbidity method with *Lactobacillus plantarum* ATCC 8014. As the result, the supernatant contained 126 mg of d-biotin per liter. Kurthia sp. 538-2A13 (DSM No. 10607) produced about 3 times as much biotin as the parent strain, Kurthia sp. 538-51F9 (DSM No. 10610), did.

Table 1 below summarizes the d-biotin productivities of the mutants so far obtained.

TABLE 1 d-Biotin Productivities of the Mutants derived from *Kurthia sp.* 538-6 (DSM No. 9454)

| Example No. | Microorganism | Resistance to antimetabolite | d-Biotin produced (mg/L) |
|---|---|---|---|
| Control strain | Kurthia sp. 538-6 (DSM No. 9454) | | <0.001 |
| 1 | Kurthia sp. 538-KA 26 (DSM No. 10609) | ACM | 3.9 |
| 2 | Kurthia sp. 538-17H4 (DSM No. 10608) | ACM, TVA | 26.3 |
| 4 | Kurthia sp. 538-51F9 (DSM No. 10610) | ACM, TVA, 80 μg/ml of MeDTB | 41.5 |

TABLE 1-continued d-Biotin Productivities of the Mutants derived from *Kurthia sp.* 538-6 (DSM No. 9454)

| Example No. | Microorganism | Resistance to antimetabolite | d-Biotin produced (mg/L) |
|---|---|---|---|
| 5 | *Kurthia sp.* 538-2A13 (DSM No. 10607) | ACM, TVA, 150 μg/ml of MeDTB | 126 |

ACM: acidomycin; TVA: 5-(2-thienyl)-valeric acid, MeDTB: α-methyl dethiobiotin

We claim:

1. An isolated microorganism which is a mutant of *Kurthia sp.* 538-6 (DSM No. 9454) and capable of fermentatively producing from about 40 mg/L to about 126 mg/L of d-biotin.

2. An isolated microorganism which is a mutant of *Kurthia sp.* 538-6 (DSM No. 9454), resistant to at least one biotin antimetabolite and capable of producing from about 4.0 mg/L to about 126 mg/L of d-biotin.

3. The microorganism according to claim 2 in which said antimetabolite is taken from the group consisting of acidomycin, 5-(2-thienyl)-valeric acid, α-methyl dethiobiotin, 2-methyl acidomycin, amiclenomycin and bisnorbiotinol.

4. The microorganism of claim 1 wherein said microorganism is *Kurthia sp.* 538-KA 26 (DSM No. 10609).

5. The microorganism of claim 1 wherein said microorganism is *Kurthia sp.* 538-17H4 (DSM No. 10608).

6. The microorganism of claim 1 wherein said microorganism is *Kurthia sp.* 538-51F9 (DSM No. 10610).

7. The microorganism of claim 1 wherein said microorganism is *Kurthia sp.* 538-2A 13 (DSM No. 10607).

8. A process for producing d-biotin which comprises:
   (a) cultivating *Kurthia sp.* 538-2A13 having the identifying characteristics of DSM No. 10607 for about 24 hours at about 28° C. in a culture media, said culture media comprising about 6% glycerol, about 5.5% proteose peptone, about 0.1% $KH_2PO_4$, about 0.05% $MgSO_4 \cdot 7H_2O$, about 0.05% $FeSO_4 \cdot 7H_2O$, about 0.001% $MnSO_4 \cdot 5H_2O$ and about one drop of antifoam CA-115;
   (b) replenishing said culture media a sterile nutrient media, said nutrient media comprising about 40% glycerol and about 20% pepteose peptone;
   (c) cultivating said replenished culture media for about 120 hours at about 28° C.; and
   (d) separating the resulting d-biotin from the culture media.

9. A process for producing d-biotin which comprises:
   (a) cultivating a microorganism selected from the group consisting of *Kurthia sp.* 538-KA 26 (DSM No. 10609), *Kurthia sp.* 538-17H4 (DSM No. 10608), *Kurthia sp.* 538-51F9 (DSM No. 10610) and *Kurthia sp.* 538-2A13 (DSM No. 10607), said organism being resistant to at least one biotin antimetabolite and capable of producing d-biotin in a medium under aerobic conditions; and
   (b) separating the resulting d-biotin from the fermentation broth.

10. The process according to claim 9, wherein at least one biotin antimetabolite is selected from the group consisting of acidomycin, 5-(2-thienyl)-valeric acid, α-methyl dethiobiotin, 2-methyl acidomycin, amiclenomycin, and bisnorbniotinol or a mixture thereof.

11. The process according to claim 9, wherein the cultivation is carried out in a medium containing an assimilable carbon source, a digestible nitrogen source, inorganic salts, and other nutrients necessary for the growth of the microorganism at a pH value of about 5.0 to about 9.0, at a temperature of about 10° C. to 40° C., and for about 1 to 10 days under aerobic conditions.

12. The process according to claim 10, wherein the cultivation is carried out in a medium containing an assimilable carbon source, a digestible nitrogen source, inorganic salts, and other nutrients necessary for the growth of the microorganism at a pH value of about 5.0 to about 9.0, at a temperature of about 10° C. to 40° C., and for about 1 to 10 days under aerobic conditions.

13. The process according to claim 12, wherein the cultivation is carried out at a pH value of 6.5 to 7.5, at a temperature of 26° C. to 30° C., and for 48 to 96 hours under aerobic conditions and the carbon source is selected from the group consisting of glycerol and glucose.

14. The process according to claim 12, wherein the cultivation is carried out at a pH value of 6.5 to 7.5, at a temperature of 26° C. to 30° C., and for 48 to 96 hours under aerobic conditions and the nitrogen source is peptone.

15. The process according to claim 12, wherein the cultivation is carried out at a pH value of 6.5 to 7.5, at a temperature of 26° C. to 30° C., and for 48 to 96 hours under aerobic conditions and the inorganic salt is selected from the group consisting of monopotassium phosphate, magenesium sulfate, ferrous sulfate and manganese sulfate or combinations thereof.

* * * * *